United States Patent [19]

Schulz et al.

[11] 4,195,186

[45] * Mar. 25, 1980

[54] PROCESS FOR PREPARING ORGANIC ACIDS

[75] Inventors: Johann G. D. Schulz, Pittsburgh; Edward T. Sabourin, Allison Park, both of Pa.

[73] Assignee: Gulf Research and Development Company, Pittsburgh, Pa.

[*] Notice: The portion of the term of this patent subsequent to Oct. 4, 1994, has been disclaimed.

[21] Appl. No.: 924,054

[22] Filed: Jul. 12, 1978

[51] Int. Cl.$^2$ .................................... C07C 51/20
[52] U.S. Cl. ............................................. 562/407
[58] Field of Search ................................. 562/407

[56] References Cited
U.S. PATENT DOCUMENTS

| | | | |
|---|---|---|---|
| 2,555,410 | 6/1951 | Howard | 562/407 |
| 2,726,262 | 12/1955 | Grosskinsky | 562/407 |
| 3,709,931 | 1/1973 | Proell et al. | 562/407 |
| 4,052,448 | 10/1977 | Schulz et al. | 562/407 |

*Primary Examiner*—Jane S. Myers

[57] ABSTRACT

A process for preparing a mixture of polycyclic aromatic polycarboxylic acids that is substantially soluble in acetone but substantially insoluble in water which comprises subjecting a slurry containing coal to reaction with aqueous nitric acid in an atmosphere containing molecular oxygen, mechanically separating the solids in the resulting slurry, extracting the resulting solids with a polar solvent to separate therefrom a mixture of polycyclic aromatic polycarboxylic acids substantially soluble in acetone but substantially insoluble in water and a mixture of polycyclic aromatic polycarboxylic acids substantially insoluble in acetone and substantially insoluble in water.

6 Claims, No Drawings

PROCESS FOR PREPARING ORGANIC ACIDS

BACKGROUND OF THE INVENTION

1. Field of the Invention

This invention relates to a process for preparing a mixture of polycyclic aromatic polycarboxylic acids that is substantially soluble in acetone but substantially insoluble in water which comprises subjecting a slurry containing coal to reaction with aqueous nitric acid in an atmosphere containing molecular oxygen, mechanically separating the solids in the resulting slurry, extracting the resulting solids with a polar solvent to separate therefrom a mixture of polycyclic aromatic polycarboxylic acids substantially soluble in acetone but substantially insoluble in water and a mixture of polycyclic aromatic polycarboxylic acids substantially insoluble in acetone and substantially insoluble in water.

2. Description of the Prior Art

In our U.S. Pat. No. 4,052,448, which is incorporated herein by reference, we disclosed a process for preparing a mixture of polycyclic aromatic polycarboxylic acids that is substantially soluble in acetone but substantially insoluble in water which involved subjecting a slurry containing coal to reaction with aqueous nitric acid, mechanically separating the solids in the resulting slurry, extracting the resulting solids with a polar solvent and then separating the polar solvent from the extract to recover the mixture of polycyclic aromatic polycarboxylic acids substantially soluble in acetone but substantially insoluble in water.

SUMMARY OF THE INVENTION

We have now found, unexpectedly, that we can greatly increase the amount of acetone-soluble, water-insoluble polycyclic aromatic polycarboxylic acids obtained in the process disclosed and claimed in said U.S. Pat. No. 4,052,448 if we carry out the nitric acid reaction therein in an atmosphere containing molecular oxygen.

The individual components of the acetone-soluble, water-insoluble polycyclic aromatic polycarboxylic acids obtained herein are believed to be composed of condensed and/or non-condensed benzene rings, with an average number of benzene rings in the individual molecules ranging from two to about 10, but generally from three to about eight. On the average, the number of carboxyl groups carried by the individual molecules will range from about four to about 10, generally from about six to about eight and the average number of nitro groups from about one to about four, generally from about two to about three. The average molecular weight of the mixture will range from about 600 to about 1500, generally from about 700 to about 1000, and the average neutral equivalent will range from about 80 to about 200, generally from about 100 to about 150. A typical analysis of the desired mixture is defined below in Table I in approximate amounts.

TABLE I

| | Weight Per Cent | |
|---|---|---|
| | Broad Range | Preferred Range |
| Carbon | 50 to 60 | 52 to 56 |
| Hydrogen | 3 to 5 | 3.7 to 4.4 |
| Nitrogen | 3 to 6 | 4 to 5 |
| Oxygen | 25 to 45 | 30 to 40 |
| Sulfur | 0.2 to 0.5 | 0.3 to 0.5 |

TABLE I-continued

| | Weight Per Cent | |
|---|---|---|
| | Broad Range | Preferred Range |
| Ash | 0.1 to 5 | 0.3 to 3 |

In the preferred procedure herein there is introduced into a reactor an aqueous solution of nitric acid and a carbonaceous material. The nitric acid can have a concentration of about 5 to about 90 percent, but preferably will be in the range of about 10 to about 70 percent. The carbonaceous material is preferably a solid in the form of a slurry, for example, an aqueous slurring containing the carbonaceous material in particulate form and from about 50 to about 90 weight percent of water.

The solid carbonaceous material that can be used herein can have the following composition on a moisture-free basis:

TABLE II

| | Weight Per Cent | |
|---|---|---|
| | Broad Range | Preferred Range |
| Carbon | 45 to 95 | 60-92 |
| Hydrogen | 2.5-7 | 4-6 |
| Oxygen | 2.0-45 | 3-25 |
| Nitrogen | 0.75-2.5 | 0.75-2.5 |
| Sulfur | 0.3-10 | 0.5-6 |

The carbon and hydrogen content of the carbonaceous material will reside primarily in multi-ring aromatic compounds (condensed and/or uncondensed), heterocyclic compounds, etc. Oxygen and nitrogen are believed to be present primarily in chemical combination. Some of the sulfur is believed to be present in chemical combination with the aromatic compounds and some in chemical combination with inorganic elements associated therewith, for example, iron and calcium.

In addition to the above the solid carbonaceous material being treated herein will also contain solid, primarily inorganic, compounds which will not be converted to the desired organic mixture claimed herein, which are termed ash and are composed chiefly of compounds of silicon, aluminum, iron and calcium, with smaller amounts of compounds of magnesium, titanium, sodium and potassium. The ash content of the carbonaceous material treated herein will amount to less than about 50 weight percent, based on the moisture-free carbonaceous material, but, in general, will amount to about 0.1 to about 30 weight percent, usually about 0.5 to about 20 weight percent.

Anthracitic, bituminous and subbituminous coal, lignitic materials, and other type of coal products referred to in ASTM D-388 are exemplary of the solid carbonaceous materials which can be treated in accordance with the process defined herein to produce the claimed organic mixture. Some of these carbonaceous materials in their raw state will contain relatively large amounts of water. These can be dried prior to use herein. The carbonaceous material, prior to use, is preferably ground in a suitable attrition machine, such as a hammermill, to a size such that at least about 50 percent of the carbonaceous material will pass through a 40-mesh (U.S. Series) sieve. As noted, the carbonaceous material is slurried in a suitable carrier, preferably water, prior to reaction with nitric acid. If desired, the carbonaceous material can be treated, prior to reaction herein, using any conventional means, to remove therefrom any materials forming a part thereof that will not be converted in reaction with nitric acid herein.

The reactant mixture in the reactor is stirred while being maintained at a temperature of about 15° to about 200° C., preferably about 50° to about 100° C., and a molecular oxygen pressure of about 14.7 to about 1470 pounds per square inch gauge (about one to about 100 kilograms per square centimeter), preferably about 73.5 to about 735 pounds per square inch gauge (about five to about 50 kilograms per square centimeter) for about 0.5 to about 15 hours, preferably about two to about six hours. In order to obtain the desired mixture herein without losing appreciable amounts of carboxyl groups on the acids that are formed during the oxidation, and to obtain the desired acids in high yields in the reactor, it is absolutely critical that the reaction conditions therein, namely nitric acid concentration, temperature, pressure of molecular oxygen and reaction time, be so correlated to minimize and, preferably, to avoid decarboxylation. Gaseous products, such as nitrogen oxides, if any, can be removed from the reaction zone.

The reaction product is removed from the reactor in any convenient manner. We have found that the reaction product is soluble in, or reactable with, sodium hydroxide. At this point it is necessary to separate the oxidized product from the water and nitric acid associated therewith. This separation must be accomplished in a manner so that the carboxyl groups are not removed from the acid product. Distillation for the removal of water will not suffice, because under the conditions required for such separation, a significant loss of carboxyl groups would occur. Accordingly, we have found that a mechanical separation will suffice. The reaction product is therefore led to a first separator which can be, for example, a filter or a centrifuge.

The solids that are recovered in the first separator, also soluble in sodium hydroxide, are led to a second separator wherein they are subjected to extraction with acetone that is introduced therein. Such separation can be carried out at a temperature of about 20° to about 60° C., preferably about 25° to about 50° C., and a pressure of about atmospheric to about 500 pounds per square inch gauge (about atmospheric to about 35 kilograms per square centimeter), preferably about atmospheric to about 100 pounds per square inch gauge (about atmospheric to about seven kilograms per square centimeter). The solid material, insoluble in acetone, is removed from the second separator by one line and the acetone solution of the desired acid mixture by another line. The acetone solution is then led to a drier or evaporator wherein acetone is separated therefrom by one line and the desired acetone-soluble, water-insoluble polyaromatic, polycarboxylic acid mixture prepared herein is recovered by another line. As before, the acid mixture in the drier must be treated by so correlating the conditions therein to remove acetone therefrom in such manner so as to minimize and, preferably, avoid, decarboxylation. The temperature can be in the range of about 10° to about 60° C., preferably about 20° to about 50° C., the pressure about 10 millimeters of mercury to about atmospheric, preferably about 30 millimeters of mercury to about atmospheric, for about 0.5 to about 24 hours, preferably about one to about five hours.

The filtrate obtained in the first separator is removed therefrom and in all cases will contain water, nitric acid and most of the inorganic material (ash) that was present in the carbonaceous charge. In addition there can also be present other oxidized material, which are primarily acetone-soluble, water-soluble organic acids.

Separation of the filtrate into its component parts can be effected as follows. It can be passed to a distillation tower maintained at a temperature of about 50° to about 100° C., preferably about 70° to about 90° C., and a pressure of about 10 millimeters of mercury to about atmospheric, preferably about 30 millimeters of mercury to about atmospheric. Under these conditions nitric acid and water are removed from the distillation tower by one line and solids by another line. The solids are led to a third separator where they are subjected to extraction with acetone introduced therein. The conditions in the third separator are similar to those used in the second separator. A mixture of acetone-soluble, water-soluble organic acids is removed from the third separator by one line and substantially all of the inorganic material that was present in the carbonaceous charge by another line.

Several runs were carried out in which a North Dakota Lignite analyzing as follows, on a substantially moisture-free basis, was subjected to oxidation: 65.03 weight percent carbon, 4.0 weight percent hydrogen, 27.0 weight percent oxygen, 0.92 weight percent sulfur, 0.42 weight percent nitrogen and 0.04 weight percent moisture. The ash was further analyzed and found to contain 43 weight percent oxygen, 7.8 weight percent sulfur and the remainder metals. In each of Runs Nos. 1, 2 and 3, 70 percent aqueous nitric acid was gradually added over a period of two hours to a stirred slurry maintained at 70° C. containing 800 grams of powdered lignite defined above (corresponding to 540 grams of moisture-free feed) and 600 grams of water. In each of these runs the pressure in the closed reactor at the beginning was atmospheric and was permitted to rise during the course of the reaction to its autogeneous pressure. In Run No. 4, otherwise similar to Runs Nos. 1, 2 and 3, molecular oxygen was also continuously introduced into the reactor to maintain therein a pressure of 500 pounds per square inch gauge (34 kilograms per square centimeter) over the course of the reaction.

At the end of the reaction period the product slurry was withdrawn from the reaction zone and filtered to obtain a solids fraction and a filtrate. The solids were extracted with acetone at atmospheric temperature and pressure. The acetone solution was then subjected to evaporation at atmospheric temperature and pressure to obtain the desired mixture herein. The acetone insoluble portion was found to be soluble in sodium hydroxide and to comprise organic acids of a relatively higher molecular weight than the acetone-soluble portion.

The work-up of the filtrate was carried out as follows. Initially the filtrate was subjected to distillation to separate unreacted nitric acid and water therefrom. The remaining solids were subjected to extraction with acetone at atmospheric temperature and atmospheric pressure. The acetone solution was dried to remove acetone therefrom, resulting in the recovery of small amounts of the acetone-soluble, water-soluble organic acids substantially completely soluble in sodium hydroxide. The residue was mainly ash. The data obtained are summarized below in Table III.

TABLE III

| | | Weight Distribution of Polycyclic Aromatic Polycarboxylic Acids | | | | |
|---|---|---|---|---|---|---|
| Run No. | Total Nitric Acid Added, Grams* | Acetone-Insoluble Water-Insoluble, Acids, Grams | Acetone-Soluble, Water-insoluble, Acids, Grams | Acetone-Soluble Water-Soluble, Acids, Grams | Total Aromatic Acids Produced Grams | Total Nitric Acid Consumed Grams |
| 1 | — | 302.9 | 142.5 | 104.0 | 549.4 | 566.9 |
| 2 | — | 107.0 | 156.0 | 174.0 | 437.0 | 872.0 |
| 3 | — | 86.0 | 109.0 | 200.0 | 395.0 | 1050.0 |
| 4 | — | 154.7 | 224.7 | 192.0 | 571.4 | 453.0 |

*On a 100 percent basis.

The results obtained above are most unusual. Doubling the amount of nitric acid in Run No. 2 over that used in Run No. 1 might have led one to expect an increase in the amount of acetone-soluble, water-insoluble acids obtained, since the latter are believed to be a higher oxidation species of the acetone-insoluble, water-insoluble species, but the amount of increase was slight and at the expense of an increased nitric acid consumption. Further increase in the amount of nitric acid introduced into the reaction zone in Run No. 3, unfortunately, greatly reduced the amount of acetone-soluble, water-insoluble acids produced, with a still greater consumption of nitric acid. However, when Run No. 1 was repeated, except that the process was conducted in an atmosphere containing molecular oxygen, the amount of acetone-soluble, water-insoluble acids produced was greatly increased with a greatly decreased nitric acid consumption.

Although we have stated above that the desired composition is acetone-soluble and we have shown the use of acetone as suitable in the process defined herein, this has been done merely as a characterization of the composition and to exemplify one embodiment of our process. Many polar solvents alone, or polar solvents in combination with other solvents, can be used in place of acetone herein. Among the polar solvents, or combination of solvents, that can be used are methanol, ethanol, isopropanol, methyl ethyl ketone, tetrahydrofuran, dioxane, cyclohexanone, tetrahydrofurfuryl alcohol, acetone in combination with methanol, methyl ethyl ketone in combination with methanol, isopropanol or water, tetrahydrofuran in combination with methanol or water, dioxane in combination with methanol or water, etc.

Obviously, many modifications and variations of the invention, as hereinabove set forth, can be made without departing from the spirit and scope thereof and, therefore, only such limitations should be imposed as are indicated in the appended claims.

We claim:

1. A process for preparing a mixture of polycyclic aromatic polycarboxylic acids that is substantially soluble in acetone but substantially insoluble in water which comprises subjecting an aqueous slurry containing coal to reaction with aqueous nitric acid having a concentration of about 5 to about 90 percent at a reaction temperature of about 15° to about 200° C. in an atmosphere containing molecular oxygen having a pressure of about 14.7 to about 1470 pounds per square inch gauge over a period of about 0.5 to about 15 hours, mechanically separating the solids in the resulting slurry, extracting the resulting solids with a polar solvent to separate therefrom a mixture of polycyclic aromatic polycarboxylic acids substantially soluble in acetone but substantially insoluble in water and a mixture of polycyclic aromatic polycarboxylic acids substantially insoluble in acetone and substantially insoluble in water.

2. The process of claim 1 wherein the aqueous nitric acid has a concentration of about 10 to about 70 percent and the reaction is carried out at a temperature of about 50° to about 100° C. and a pressure of molecular oxygen of about 73.5 to about 735 pounds per square inch gauge for about two to about six hours.

3. The process of claim 1 wherein said polar solvent is acetone.

4. The process of claim 1 wherein the mechanical separation is effected by filtration.

5. The process of claim 1 wherein the polar solvent is separated from the extract by drying.

6. The process of claim 1 wherein the coal is lignite.

* * * * *